United States Patent
Ganciu-Petcu et al.

(10) Patent No.: US 8,581,494 B2
(45) Date of Patent: Nov. 12, 2013

(54) DISCHARGE LAMP FOR GDS WITH AN AXIAL MAGNETIC FIELD

(75) Inventors: Mihai Ganciu-Petcu, Bucarest (RO); Virgil Mircea Udrea, Bucarest (RO); Agnes Tempez, Massy (FR); Patrick Chapon, Villebon sur Yvette (FR)

(73) Assignee: Horiba Jobin Yvon SAS, Longjumeau (FR)

( * ) Notice: Subject to any disclaimer, the term of this patent is extended or adjusted under 35 U.S.C. 154(b) by 295 days.

(21) Appl. No.: 13/147,906

(22) PCT Filed: Feb. 10, 2010

(86) PCT No.: PCT/FR2010/050226
§ 371 (c)(1),
(2), (4) Date: Aug. 4, 2011

(87) PCT Pub. No.: WO2010/092301
PCT Pub. Date: Aug. 19, 2010

(65) Prior Publication Data
US 2011/0291567 A1    Dec. 1, 2011

(30) Foreign Application Priority Data
Feb. 11, 2009 (FR) .................... 09 50848

(51) Int. Cl.
*H01J 7/24* (2006.01)
(52) U.S. Cl.
USPC ............ 315/111.01; 315/111.41; 315/111.71; 313/155; 313/231.31
(58) Field of Classification Search
USPC ............. 315/111.01, 111.11, 111.21, 111.31, 315/111.41, 111.71; 313/153, 155, 231.01, 313/231.31
See application file for complete search history.

(56) References Cited

U.S. PATENT DOCUMENTS

| | | | | |
|---|---|---|---|---|
| 5,374,327 A | * | 12/1994 | Imahashi et al. | 438/9 |
| 5,733,820 A | * | 3/1998 | Adachi et al. | 438/719 |
| 5,986,747 A | * | 11/1999 | Moran | 356/72 |
| 5,988,103 A | * | 11/1999 | Fetherston et al. | 118/723 E |
| 6,876,155 B2 | * | 4/2005 | Howald et al. | 315/111.51 |

(Continued)

OTHER PUBLICATIONS

Heintz M. J. et al. "Design and Characterization of a planar magnetron radiofrequency glow discharge source for atomic emission spectrometry" Spectrochimica Acta. Part B: Atomic Spectroscopy, New Your, NY, US, US, vol. 50, No. 9, Aug. 1, 1995, pp. 1109-1124, XP004727009, ISSN: 0584-8547, figures 1, 2.

(Continued)

*Primary Examiner* — Jason M Crawford
(74) *Attorney, Agent, or Firm* — Young & Thompson

(57) ABSTRACT

A glow discharge spectrometer discharge lamp includes: a lamp body having a vacuum enclosure connected to pump elements and to injector elements for injecting an inert gas into the enclosure; a hollow cylindrical first electrode of longitudinal axis X-X'; a second electrode for receiving a sample for analysis and for holding the sample facing one end of the cylindrical electrode; electric field generator including an applicator for applying to the terminals of the electrodes an electric field that is continuous, pulsed, radiofrequency, or hybrid, and suitable for generating a glow discharge plasma in the presence of the gas; coupler elements for coupling the discharge lamp to a spectrometer suitable for measuring at least one component of the plasma; and magnetic field generator elements for generating a magnetic field having field lines oriented along the axis X-X', the magnetic field being uniform in orientation and in intensity over an area of the sample that is not less than the inside area of the hollow cylindrical electrode as projected along the direction X-X'.

19 Claims, 4 Drawing Sheets

(56) References Cited

U.S. PATENT DOCUMENTS 7,453,059 B2 * 11/2008 Koo et al. .................. 250/287
2001/0010255 A1 8/2001 Kijima

OTHER PUBLICATIONS

International Search Report, dated Apr. 27, 2010, from corresponding PCT application.

* cited by examiner

DISCHARGE LAMP FOR GDS WITH AN AXIAL MAGNETIC FIELD

The present invention relates to a discharge lamp for a glow discharge spectrometer (GDS).

A glow discharge spectrometer serves to analyze the chemical composition of a sample that is subjected to a plasma. The plasma ablates the surface of the sample. A mass spectrometer and/or an optical spectrometer is/are used for identifying and quantifying chemical elements incorporated in the plasma during ablation. Glow discharge spectrometers thus make it possible to analyze accurately materials that are thick or that are in thin layers (layers of thickness in the range a few tens of nanometers to a few tens of micrometers). Furthermore, prolonged exposure of the sample to the ablation plasma produces an erosion crater in depth. Analyzing the plasma as a function of the duration of ablation thus makes it possible to determine the composition of the sample with depth resolution, providing erosion takes place by etching into the sample at a uniform rate, i.e. providing the ablation crater has a flat bottom.

In a GDS apparatus, the plasma is obtained by applying an electric field (which may be DC, radiofrequency (RF), and optionally pulsed) in a discharge lamp comprising an enclosure containing an inert gas (e.g. argon). The sample is generally placed facing an anode tube and the electric power (e.g. RF power) is applied by means of an applicator in contact with the sample. Glow discharge spectrometers give good results in particular with samples on a support that is conductive or semiconductive (e.g. silicon), since they enable good coupling of the electric field in the plasma. However, when a sample is on an insulating substrate or has thick dielectric layers (e.g. glass or ceramic having a thickness of several millimeters), the plasma gives rise to heating of the sample that can lead to its destruction. Furthermore, the flanks of the erosion crater are generally clearly sloping relative to the surface of the sample, which is harmful for depth resolution of the GDS.

Saprykin (Fresenius J. Anal. Chem., 355, pp. 831-835, 1996) describes a glow discharge lamp having superposed therein an RF electric field and a magnetic field with its field lines orientated so as to confine the electrons of the plasma in the vicinity of the surface of a non-conductive sample (glass having a thickness of 1 millimeter (mm)). The device described in the Saprykin publication has annular magnets placed behind the sample. The magnetic field of several hundreds of gauss creates field lines on the sample that are in the form of closed loops. The superposition of the electric field (E) and the magnetic field (B) enables the rate of ablation to be increased, but produces an erosion crater that is annular, and with a bottom that is not flat, as would be desirable.

Furthermore, glow discharge spectrometry is difficult to apply with samples that are very thin or on a support that is fragile (e.g.: polymer films having a thickness of a few tens of micrometers), since they do not withstand the ablation plasma.

In order to reduce the heating of samples subjected to an ablation plasma, various solutions are used. A first solution relies on a powerful cooling system being used, e.g. by circulating liquid nitrogen behind the sample carrier. Cooling enables results to be obtained on certain samples, but it requires equipment to be used that is onerous and expensive, and also requires a connection with a source of cooling fluid.

Another solution for reducing the heating of samples consists in reducing the duration of exposure to the plasma by using a pulsed RF field (at a frequency of kilohertz (kHz) order, for example). Under certain circumstances, a pulsed field enables heating to be reduced, but it does not enable the shape of the ablation crater to be significantly improved. Furthermore, certain polymer samples are extremely fragile and simply cannot withstand a pulsed RF field.

An object of the present invention is to improve the sensitivity and the depth resolution of a glow discharge spectrometer, while reducing the heating of the samples as induced by the plasma of the GDS.

More particularly, the invention provides a glow discharge spectrometer discharge lamp comprising: a lamp body having a vacuum enclosure connected firstly to pump means and secondly to injector means for injecting an inert gas into said enclosure; a hollow cylindrical first electrode of longitudinal axis X-X'; a second electrode suitable for receiving a sample for analysis and for holding the sample facing one end of the hollow cylindrical electrode; electric field generator means comprising an applicator for applying to the terminals of said electrodes an electric field that is continuous (DC), pulsed, radiofrequency (RF), or hybrid, and that is suitable for generating a glow discharge plasma in the presence of said gas; coupler means for coupling the discharge lamp to a spectrometer that is suitable for measuring at least one component of said plasma; and magnetic field generator means for generating a magnetic field. According to the invention, the magnetic field generator means are suitable for generating a magnetic field having field lines that are oriented along the axis X-X', said magnetic field being uniform in intensity and in orientation over an area of the sample that is not less than the inside area of the hollow cylindrical electrode as projected along the direction X-X'.

In various embodiments of the invention, the magnetic field generator means comprise:
- at least one magnet arranged behind the second electrode, with the axis joining its poles being parallel to the axis X-X' and with its dimensions in directions transverse to the axis X-X' being greater than the projected inside area of the hollow cylindrical electrode; and/or
- a magnet in the form of a solid cylinder of axis X-X', said magnet being arranged behind the sample-carrier electrode; and/or
- at least one magnet of annular shape arranged around the hollow cylindrical electrode and for which the axis joining its poles is parallel to the axis X-X' of said electrode; and/or
- an electromagnetic coil of axis parallel to the axis X-X'.

In a particular embodiment of the invention, the material of said magnet(s) is NbFeB.

In a preferred embodiment of the invention, the magnetic generator means comprise one or more magnets arranged in a metal coupler and held in the coupler by electrically insulating parts, the coupler being connected firstly to the second electrode and secondly to the electric field applicator in such a manner that the magnetic axis of the magnet(s) coincide(s) with the axis X-X'.

In a particular embodiment, the discharge lamp of the invention includes cooling means suitable for cooling the magnetic field generator means.

In a preferred embodiment of the invention, the magnetic field generator means present dimensions extending transversely relative to the axis X-X' that are greater than the projected inside area of the hollow cylindrical electrode so as to generate a magnetic field that is uniform in intensity and in orientation over the area of the sample facing the end of the hollow cylindrical electrode.

In a particular embodiment, the discharge lamp of the invention includes means for measuring the intensity of the magnetic field and suitable for comparing the intensity of the magnetic field at the sample with a predetermined threshold.

The invention also provides a method of improving a glow discharge spectrometer discharge lamp, the method comprising the following simultaneous steps of:

applying a continuous, pulsed, RF, or hybrid electric field to the terminals of the electrodes of a discharge lamp, and suitable for generating a plasma for ablating the surface of a sample; and applying an axial magnetic field of field lines parallel to the axis X-X' of the hollow cylindrical electrode of said discharge lamp, said magnetic field being uniform in orientation and in intensity over an area of the sample that is not less than the inside area of the hollow cylindrical electrode as projected along the direction X-X'.

The invention applies in particular to GDS analysis of samples that are semiconductive or non-conductive.

The following description, given by way of non-limiting example, makes it easier to understand how the invention can be implemented and is given with reference to the accompanying drawings, in which.

Figure 4:
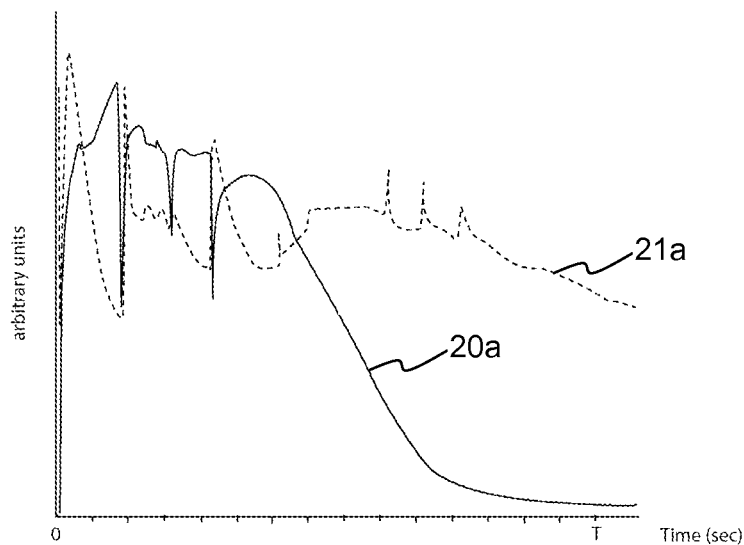
Figure 5:
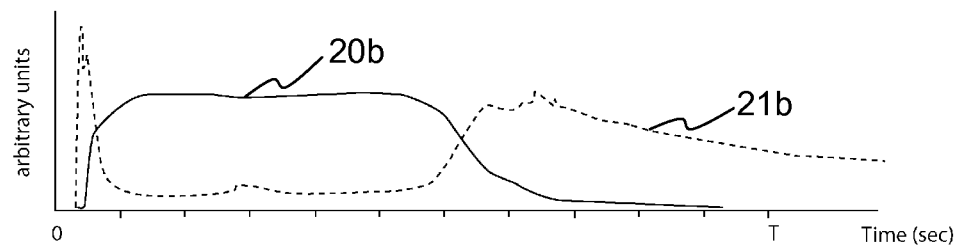
Figure 6:
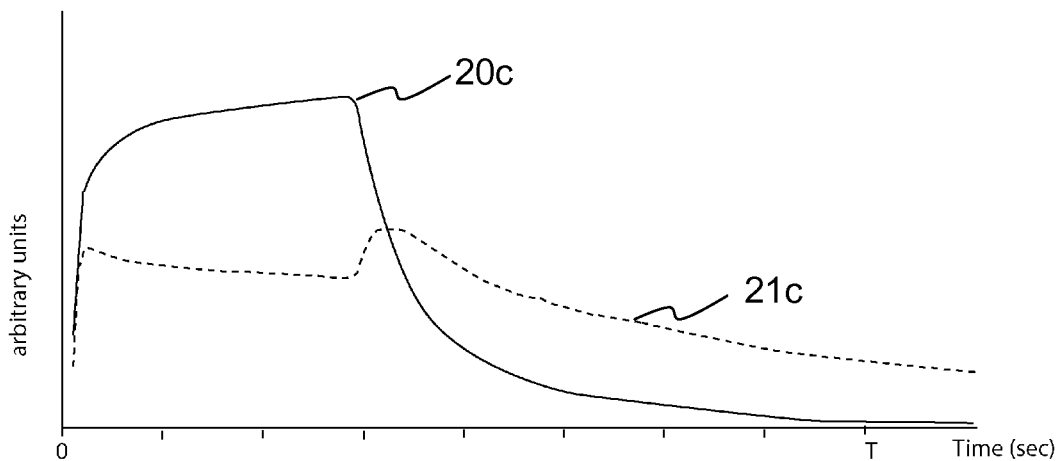
Figure 7:
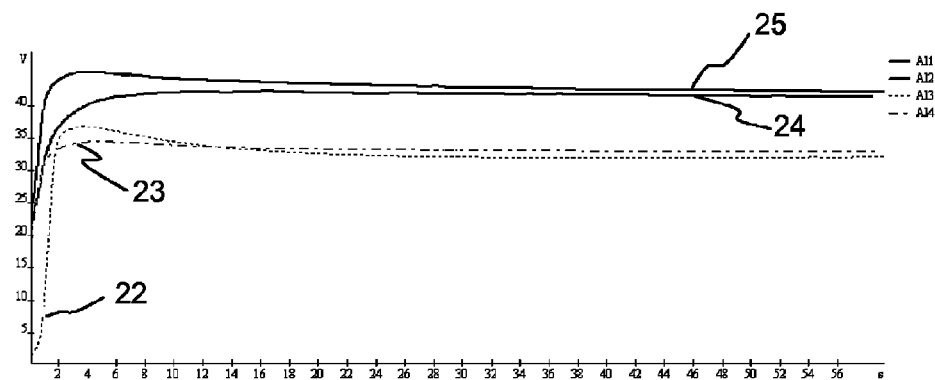
Figure 8:
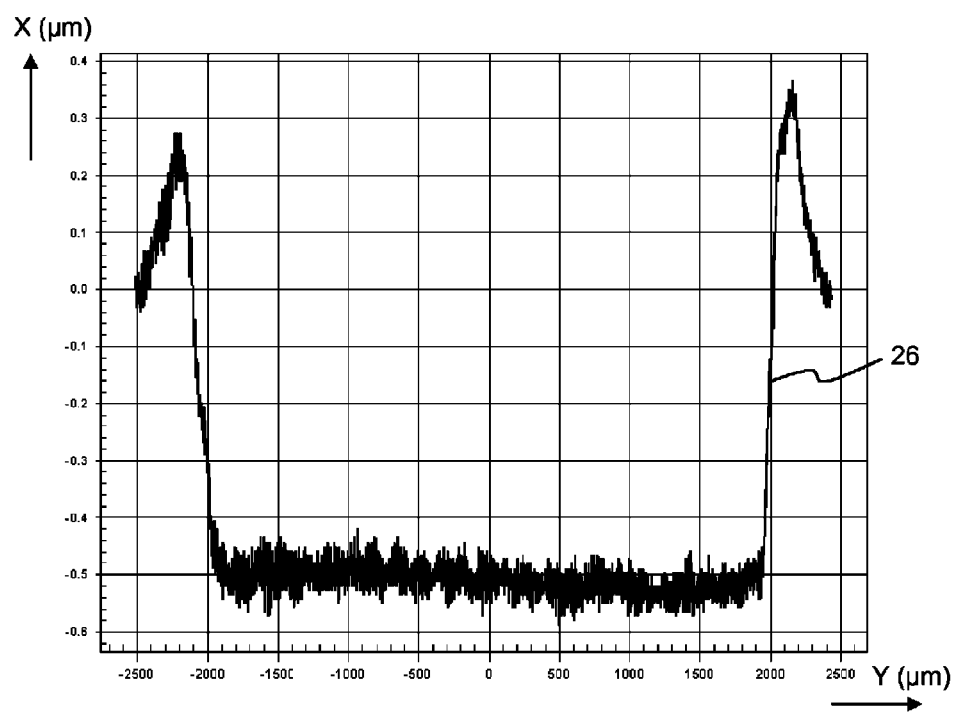

FIG. 4 plots GDS analysis curves relating to a first sample and obtained by means of a prior art glow discharge spectrometer;

FIG. 5 plots curves of GDS analysis of a sample similar to that of FIG. 4, and obtained by means of a prior art glow discharge spectrometer in which the sample carrier is cooled with liquid nitrogen;

FIG. 6 plots curves of GDS analysis of a sample similar to that of FIGS. 4 and 5, but obtained by means of a glow discharge spectrometer of the invention;

FIG. 7 is a single graph having plotted thereon curves of GDS analysis of samples of a second type obtained by means of a prior art glow discharge spectrometer and a glow discharge spectrometer of the invention; and FIG. 8 is a profile-measurement curve of an ablation crater in a thick glass sample as obtained by analysis using a glow discharge spectrometer of the invention.

Figure 1:
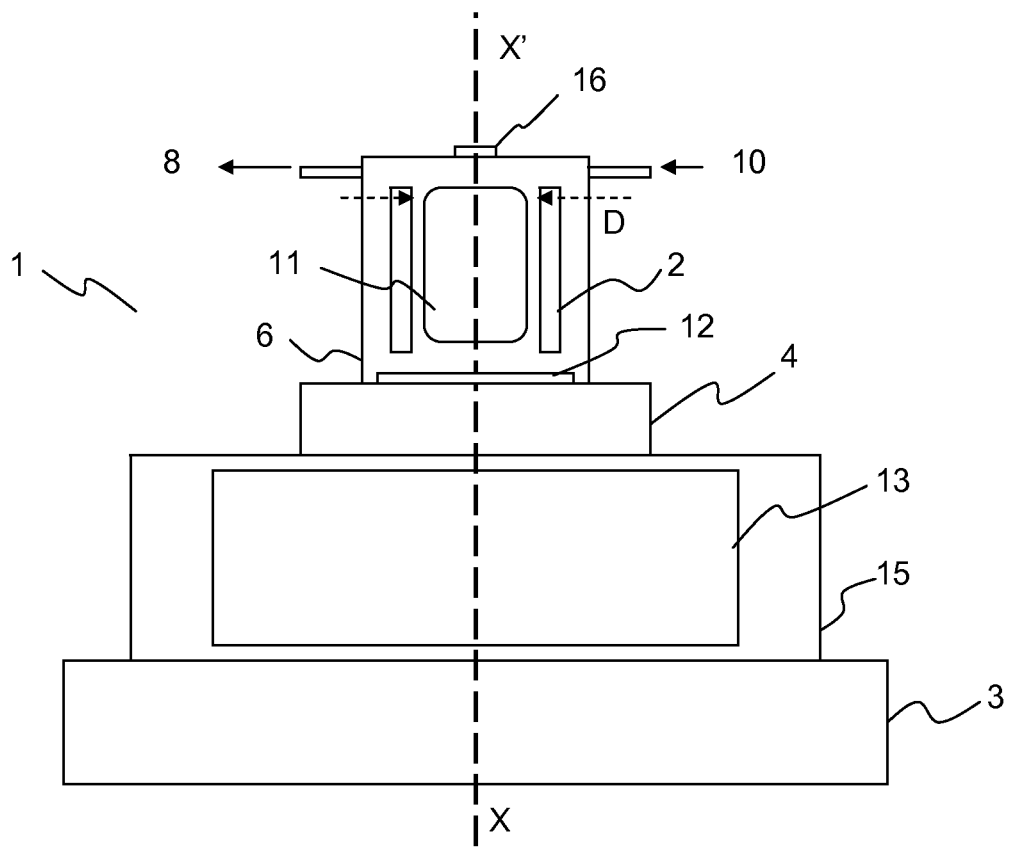
FIG. 1 is a diagrammatic axial section view of a GDS discharge lamp of the invention.

FIG. 1 is a diagrammatic axial section of a GDS discharge lamp 1 in an embodiment of the invention. The discharge lamp 1 includes a vacuum enclosure 6 connected to a pump 8 and to a source 10 of inert gas (e.g. argon). The discharge lamp 1 includes a hollow cylindrical first electrode 2 and a second electrode 4 that serves to carry the sample. The axis X-X' of the cylindrical electrode 2 is the axis of the discharge lamp. A sample 12 is held on the electrode 4 facing the anode tube 2. For samples that are plane, the electrode 4 is generally plane. An RF applicator 3 applies an RF electric field to the electrode 4, the electrode 2 being connected to ground. An ablation plasma 11 forms inside the anode and etches the surface of the sample 12 that is exposed to the plasma facing the end of the hollow cylindrical anode 2. The vacuum enclosure includes coupling means 16 for coupling an optical spectrometer or a mass spectrometer in order to analyze the chemical species incorporated in the plasma while etching the sample 12. When an optical spectrometer is used, the coupling means 16 comprise a window or a lens so as to enable a portion of the optical intensity of the emission plasma to be received. When a mass spectrometer is used, the coupling means 16 comprise a small opening leading to a vacuum chamber connected to the mass spectrometer so that the spectrometer measures a fraction of the components of the plasma.

In the example shown in FIG. 1, the discharge lamp 1 includes a magnet 13 having its poles lying on an axis that coincides with the axis X-X' of the lamp. The magnet 13 generates an axial magnetic field of field lines that are practically parallel to the axis X-X' over an area of the sample 12 that is not less than the inside area of the anode 2 projected onto the sample along the direction X-X', said magnetic field being uniform in orientation and in intensity over said projected area. In this document, the term "generally uniform" is used of a magnetic field in which intensity may vary by up to ±10% and orientation may vary by up to ±5° relative to the axis X-X'. The magnet 13 of FIG. 1 is placed in a coupler 15 that is in electrical contact firstly with the sample-carrier electrode 4 and secondly with the electric field RF applicator 3. The coupler 15 conducts electricity between the applicator 3 and the electrode 4. The magnet 13 is electrically isolated from the metal housing.

Figure 2:
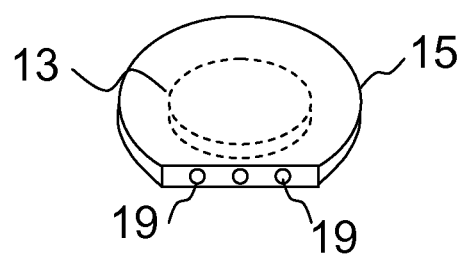
FIG. 2 is a perspective view of an RF-magnetic coupler in an embodiment of the invention.

FIG. 2 is a diagram of a magnetic-RF coupler 15 that has one or more magnets 13 of polar axis X-X'. The magnets 13 are preferably NdFeB magnets placed in a metal structure and held by insulators in order to provide good RF coupling between the RF applicator 3 and the sample. The magnets 13 are preferably of the solid disk type, but they could optionally be of same other shape (e.g. rectangular), while nevertheless serving to generate an axial magnetic field inside the anode 2. Another possible shape for the magnet 13 is for example a toroidal shape (perforated disk) enabling the magnet(s) to be arranged around the anode 2. Such a shape enables the magnet 13 to be incorporated in the structure of the discharge lamp 1 without modifying the sample carrier 4 or the RF applicator 3 behind the sample 12.

In any event, it is desirable to avoid the magnets 13 being heated, since that would lead to rapid demagnetization thereof. A conventional cooling system may advantageously be mounted so as to cool the magnets 13 of the device. The coupler 15 shown in FIG. 2 includes cooling means 19, e.g. for circulating a fluid. In another embodiment (not shown), the magnetic-RF coupler 15 may be incorporated in the RF applicator 3.

The intensity of the magnetic field at the sample is at least several hundreds of gauss. It is desirable periodically to inspect the intensity of the magnetic field in order to verify that it remains within the normal operating range of the magnetic-RF coupler 15. This verification may be performed with a tesla meter that gives an absolute measurement, or merely with a magnetic field detector that is external or arranged inside the coupler 15 and that serves to make sure that the field exceeds a certain minimum value in order to obtain a coupling effect in the plasma.

Figure 3:
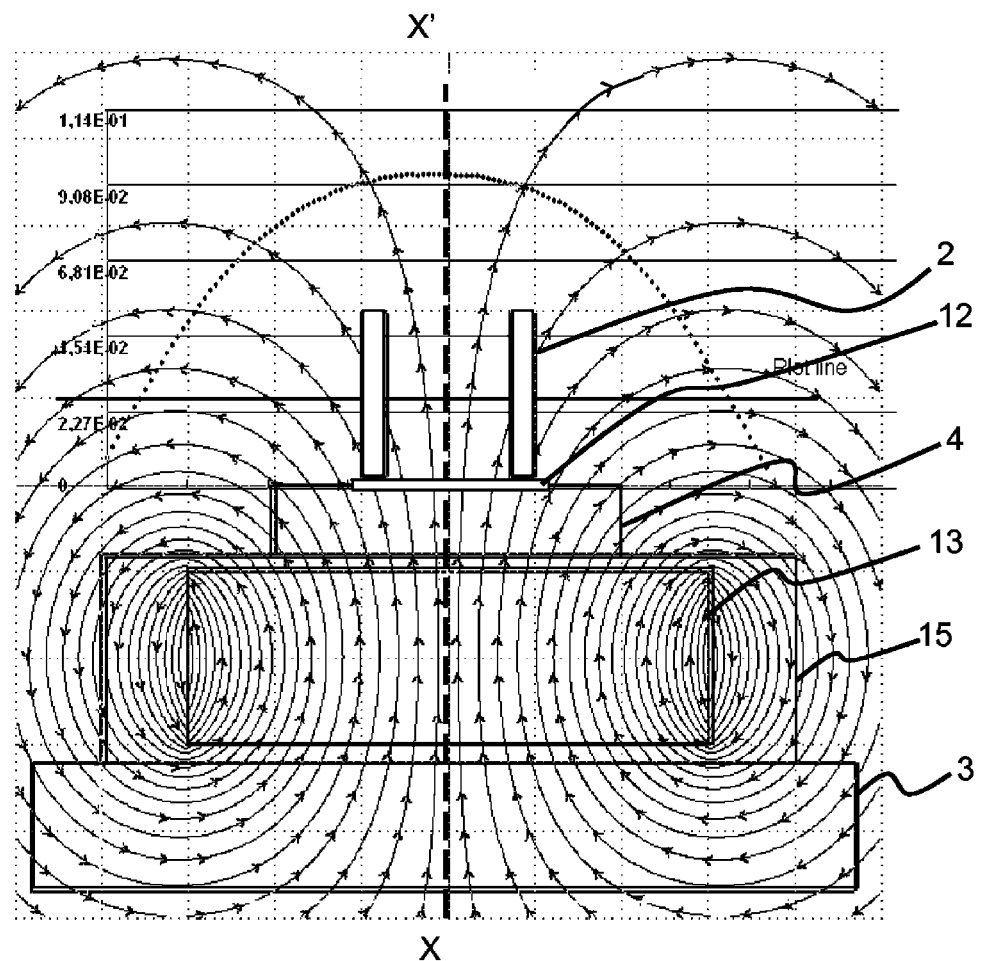
FIG. 3 shows a simulation of magnetic field lines in a GDS discharge lamp of the invention, shown in section view.

FIG. 3 shows a simulation of magnetic field lines in a GDS discharge lamp including an RF applicator and a magnetic coupler 15 as described with reference to FIGS. 1 and 2. At the sample 12, facing the end of the anode 2, the magnetic field lines are practically parallel to the axis X-X' and of intensity that is practically uniform.

By way of example, the axial magnetic field may be generated by one or more magnets 13 placed behind the sample and the sample carrier 4.

The size of the magnets 13 must be considerably greater than the inside area of the cylindrical anode 2 as projected along the axis X-X' in order to ensure that the magnetic field is uniform in orientation and intensity over the surface of the sample 12 facing the anode 2 and exposed to the ablation plasma 11. The dimensions of the magnets 13 used may be selected as a function of applications, but the recommended device consists in having a single type of magnet 13 of dimensions that are optimized for a wide range of applications. In the embodiment shown diagrammatically in FIGS. 1 to 3, the electrode 2 is a cylinder of circular section with an inside diameter of 4 mm. The magnet 13 used is a solid disk having a diameter of about 28 mm and it generates a magnetic field of about 600 gauss (G) at the surface of the sample in contact with the ablation plasma.

FIGS. 4 to 6 show the results of GDS analysis obtained on a sample 12 of the same type comprising a polymer film covered on one face with a thin layer of metal and subjected to an RF plasma, respectively in accordance with the prior art (FIGS. 4 and 5) and in accordance with the invention (FIG. 6). Polymer films are extremely fragile and they are generally carbonized during plasma exposure in a GDS apparatus. The curves of FIGS. 4 to 6 show the glow discharge optical spectrometry measurements that correspond respectively to measuring a component made of metal (curves 20*a*, 20*b*, 20*c*) and of carbon (curves 21*a*, 21*b*, 21*c*).

The curves of FIG. 4 were obtained in a prior art discharge lamp in which a DC electric field was applied to the sample 12. The sample carrier was not cooled. Under such conditions, the polymer sample was subjected to a large amount of heating by the plasma. The carbon emission peaks (curve 21*a*) correspond to instants at which part of the polymer sample was burning, thereby producing intense emission peaks. The sample was thus severely damaged by the GDS measurement and the duration of the measurement was very short. The curve measuring the metal layer (curve 20*a*) also includes peaks showing that ablation did not provide resolution in depth.

The curves of FIG. 5 correspond to the same optical spectrometry measurements, in a discharge lamp in which a DC electric field was applied to the sample 12 and in which the sample carrier was cooled by liquid nitrogen. The disappearance of the peaks in the curves 21*a* and 21*b* indicates that it was the excessive heating of the sample that was responsible for the peaks in the curves 20*a* and 21*a* in FIG. 4. It was possible to measure the metal layer (curve 20*b*) and the polymer substrate (curve 21*b*) without damaging the sample. Nevertheless, the transition between the metal and polymer layers was quite spread out, indicating erosion both in the metal layer and in the substrate, and impeding analysis that is accurate in terms of resolution in depth. In addition, a setup that includes liquid nitrogen cooling is complex and burdensome and difficult to adapt to certain samples.

The curves of FIG. 6 correspond to the same optical spectrometry measurements but in a discharge lamp where a DC electric field and an axial magnetic field were applied simultaneously to the sample 12, but without cooling the sample carrier. The non-pulsed mode of operation was selected since that corresponds to the most unfavorable circumstances concerning heating. It can be seen that there are no peaks in the curves 20*c* and 21*c*, which means that the axial magnetic field made it possible to limit heating of the sample. In addition, the signal-to-noise ratio of the curves 20*c* and 21*c* is considerably improved compared with the curves 20*b* and 21*b* of FIG. 5. The interface between the polymer support and the metal layer as etched initially on exposure to the plasma, can be observed more clearly, which corresponds to better resolution in depth. The coupling of an RF electric field with a magnetic field thus enables a fragile polymer sample to be subjected to GDS measurement, where such a measurement used to be difficult without a powerful cooling system, and the coupling also enables an excellent signal-to-noise ratio to be obtained with good resolution in depth.

The apparatus of the invention is thus also suitable for new applications for GDS analysis, for example using thick insulating samples. It is generally not possible to measure thick insulating samples by GDS while applying an RF electric field, even a pulsed field, because of the poor electric coupling between the electrode and the plasma. Furthermore, the high degree of heating that is induced by the GDS on insulating samples, e.g. glass samples, can lead to the samples bursting.

FIG. 7 shows an example of GDS analysis obtained using various samples of alumina ($Al_2O_3$) that were subjected respectively to a continuous RF plasma (curves 22 and 23) and to an RF plasma coupled to an axial magnetic field (curves 24 and 25). Two measurements were taken in each circumstance in order to evaluate the reproducibility of the measurement. It can be seen that curves 24 and 25 are at a level that is about 30% higher than the level of the curves 22 and 23. This increase is representative of better electromagnetic coupling in the plasma, thereby enabling greater power to be coupled effectively in the plasma. This better coupling gives rise to faster erosion, and thus to greater signal intensity. In this application, it can also be seen that there is an improvement in the signal-to-noise ratio of the GDS measurement.

An effect of applying an axial magnetic field is to make it possible to analyze samples on a substrate that is insulating, even if it is thick (several millimeters).

Thus, FIG. 8 shows the profile 26 of an ablation crater in a thick glass sample after the sample was exposed to an RF plasma coupled to an axial magnetic field. The profile 26 of FIG. 8 shows a crater that is several micrometers deep with a bottom that is almost perfectly flat. The etching plasma thus made it possible to obtain anisotropic erosion in a volume of the glass substrate. Such a flat-bottom crater has never been obtained in the past in a GDS discharge lamp making use solely of a continuous or pulsed RF electric field with this type of sample.

It can be seen that the electromagnetic coupling is performed through the insulating sample with improved efficiency. Furthermore, a remarkable effect of the uniform axial magnetic field is to produce an ablation crater having a bottom that is practically flat. This property makes it possible to analyze the composition of a sample by means of GDS with excellent depth resolution and over a considerable etching depth.

The only drawback of the device of the invention may be very slight erosion of the anode at the beginning of discharge (identical to that which is observed when the anode is of small diameter).

To summarize, the application of an axial magnetic field serves to improve several aspects of a glow discharge spectrometer.

Firstly, an improvement is observed in the coupling of the electromagnetic field in the plasma when the samples for analysis are insulating or contain thick dielectric layers (e.g. glass 1 centimeter (cm) thick).

The distribution of the plasma is modified by simultaneously applying an electric field on an axial magnetic field. Unlike prior devices that sought to increase the density of the plasma in the vicinity of the surface of the sample, in the device of the invention it is observed that the plasma is more extensive along the axis of the anode 2 and more confined radially in directions perpendicular to the axis X-X'.

In order to obtain a plasma with stable erosion it is necessary to go from the so-called "alpha" regime (high impedance regime) to a so-called "gamma" regime (low impedance regime) which implies forming a thin sheet with a continuous electric field perpendicular to the surface of the sample.

Because an axial magnetic field is applied, plasma losses to the walls of the anode are minimized: plasma electrons are constrained to turn around the magnetic field lines and they are thus lost by diffusion more slowly.

The plasma confinement induced by the axial magnetic field thus makes it possible to obtain the alpha-gamma transition at lower RF power and consequently with a heat budget that is more favorable for the dielectric or semiconductive sample.

The improvement in the coupling thus makes it possible to work at a lower applied power, or for identical applied power, to reduce the heating of the sample (less heating due to collision with fast neutral elements, since the density thereof is reduced in the vicinity of the sample).

The invention also makes new applications possible for glow discharge spectrometry with certain samples that are thin and/or fragile since the device of the invention serves to reduce the destructive effects of a glow discharge on such samples.

The invention makes it possible to improve significantly firstly the signal-to-noise ratio of GDS measurements, and secondly the depth resolution of such measurements, by obtaining an erosion crater that has a flat bottom. The improvement in these features is particularly important for semiconductive or non-conductive samples.

The invention makes it possible to enlarge the field of application of GDS to insulating samples or to samples that include insulating layers, and also to samples that are thin and/or fragile.

The invention claimed is:

1. A glow discharge spectrometer discharge lamp (1) comprising:
   a lamp body having a vacuum enclosure (6) connected firstly to pump means (8) and secondly to injector means (10) for injecting an inert gas into said enclosure (6);
   a hollow cylindrical first electrode (2) of longitudinal axis X-X';
   a second electrode (4) suitable for receiving a sample (12) for analysis and for holding the sample (12) facing one end of the cylindrical electrode (2);
   electric field generator means comprising an applicator (3) for applying to the terminals of said electrodes (2 and 4) an electric field that is continuous, pulsed, radiofrequency (RF), or hybrid, and that is suitable for generating a glow discharge plasma (11) in the presence of the gas (10);
   coupler means (16) for coupling the discharge lamp to a spectrometer that is suitable for measuring at least one component of said plasma (11); and
   magnetic field generator means for generating a magnetic field;
   the lamp being characterized in that:
   the magnetic field generator means are suitable for generating a magnetic field having field lines that are oriented along the axis X-X', said magnetic field being uniform in orientation and in intensity over an area of the sample (12) that is not less than the inside area of the hollow cylindrical electrode (2) as projected along the direction X-X'.

2. A discharge lamp according to claim 1, characterized in that the magnetic field generator means comprise at least one magnet (13) arranged behind the electrode (4), with the axis joining its poles being parallel to the axis X-X' and with its dimensions in directions transverse to the axis X-X' being greater than the projected inside area of the electrode (2).

3. A discharge lamp according to claim 2, characterized in that the magnetic field generator lines comprise a magnet (13) in the form of a solid cylinder of axis X-X' and arranged behind the electrode (4).

4. A discharge lamp according to claim 2, characterized in that the magnetic field generator means comprise at least one magnet (13) of annular shape arranged around the hollow cylindrical electrode (2) and for which the axis joining its poles is parallel to the axis X-X' of said electrode (2).

5. A discharge lamp according to claim 2, characterized in that the magnetic field generator means comprise one or more NbFeB magnets.

6. A discharge lamp according to claim 2, characterized in that the magnetic generator means comprise one or more magnets (13) arranged in a metal coupler (15) and held in said coupler (15) by electrically insulating parts, said coupler (15) being connected firstly to the second electrode (4) and secondly to the electric field applicator (3) in such a manner that the magnetic axis of said magnet(s) (13) coincide(s) with the axis X-X'.

7. A discharge lamp according to claim 2, characterized in that the magnetic field generator means comprise an electromagnetic coil of axis parallel to the axis X-X'.

8. A discharge lamp according to claim 2, characterized in that it includes cooling means suitable for cooling the magnetic field generator means.

9. A discharge lamp according to claim 2, characterized in that the magnetic field generator means present dimensions extending transversely relative to the axis X-X' that are greater than the projected inside area of the hollow cylindrical electrode (2) so as to generate a magnetic field that is uniform in intensity and in orientation over the area of the sample (12) facing the end of said electrode (2).

10. A discharge lamp according to claim 2, characterized in that it includes means for measuring the intensity of the magnetic field and suitable for comparing the intensity of the magnetic field at the sample (12) with a predetermined threshold.

11. A discharge lamp according to claim 1, characterized in that the magnetic field generator lines comprise a magnet (13) in the form of a solid cylinder of axis X-X' and arranged behind the electrode (4).

12. A discharge lamp according to claim 1, characterized in that the magnetic field generator means comprise at least one magnet (13) of annular shape arranged around the hollow cylindrical electrode (2) and for which the axis joining its poles is parallel to the axis X-X' of said electrode (2).

13. A discharge lamp according to claim 1, characterized in that the magnetic field generator means comprise one or more NbFeB magnets.

14. A discharge lamp according to claim 1, characterized in that the magnetic generator means comprise one or more magnets (13) arranged in a metal coupler (15) and held in said coupler (15) by electrically insulating parts, said coupler (15) being connected firstly to the second electrode (4) and secondly to the electric field applicator (3) in such a manner that the magnetic axis of said magnet(s) (13) coincide(s) with the axis X-X'.

15. A discharge lamp according to claim 1, characterized in that the magnetic field generator means comprise an electromagnetic coil of axis parallel to the axis X-X'.

16. A discharge lamp according to claim 1, characterized in that it includes cooling means suitable for cooling the magnetic field generator means.

17. A discharge lamp according to claim 1, characterized in that the magnetic field generator means present dimensions extending transversely relative to the axis X-X' that are greater than the projected inside area of the hollow cylindrical electrode (2) so as to generate a magnetic field that is uniform in intensity and in orientation over the area of the sample (12) facing the end of said electrode (2).

18. A discharge lamp according to claim 1, characterized in that it includes means for measuring the intensity of the magnetic field and suitable for comparing the intensity of the magnetic field at the sample (12) with a predetermined threshold.

19. A method of improving a glow discharge spectrometer discharge lamp (1), the method comprising the steps of:

applying a continuous, pulsed, RF, or hybrid electric field to the terminals of the electrodes (2, 4) of a discharge lamp according to claim 1, and suitable for generating a plasma for ablating the surface of a sample (12); and characterized in that it includes the step of:

simultaneously applying an axial magnetic field of field lines parallel to the axis X-X' of the hollow cylindrical electrode (2) of said discharge lamp, said magnetic field being uniform in orientation and in intensity over an area of the sample (12) that is not less than the inside area of the cylindrical electrode (2) as projected along the direction X-X'.

\* \* \* \* \*